(12) United States Patent
Okuyama et al.

(10) Patent No.: US 7,522,703 B2
(45) Date of Patent: Apr. 21, 2009

(54) AEROSOL PARTICLE CHARGING DEVICE

(75) Inventors: Kikuo Okuyama, Higashihiroshima (JP); Manabu Shimada, Higashihiroshima (JP); Yosio Ohtani, Kanazawa (JP); Norikazu Namiki, Kanazawa (JP); Toshihiko Hino, Hamamatsu (JP)

(73) Assignees: Kanomax Japan Incorporated, Suita (JP); Hamamatsu Photonics K.K., Hamamatsu (JP)

( * ) Notice: Subject to any disclaimer, the term of this patent is extended or adjusted under 35 U.S.C. 154(b) by 496 days.

(21) Appl. No.: 10/521,173

(22) PCT Filed: Jul. 16, 2003

(86) PCT No.: PCT/JP03/09055

§ 371 (c)(1),
(2), (4) Date: Aug. 30, 2005

(87) PCT Pub. No.: WO2004/008464

PCT Pub. Date: Jan. 22, 2004

(65) Prior Publication Data

US 2006/0108537 A1    May 25, 2006

(30) Foreign Application Priority Data

Jul. 17, 2002   (JP)  ............................. 2002-208031

(51) Int. Cl.
G21K 5/10    (2006.01)
(52) U.S. Cl. ............................ 378/66; 361/226; 250/423 R; 250/435

(58) Field of Classification Search ................ 222/192; 250/281–282, 286–288, 423 F, 423 P, 423 R, 250/424, 435; 378/66, 119, 210; 361/225–228, 361/230–235
See application file for complete search history.

(56) References Cited

U.S. PATENT DOCUMENTS

| 3,171,028 | A | * | 2/1965 | Lovelock | 250/373 |
| 3,653,185 | A | * | 4/1972 | Scott et al. | 96/16 |
| 3,845,301 | A | * | 10/1974 | Wernlund et al. | 250/287 |
| 4,230,946 | A | * | 10/1980 | Wells et al. | 250/425 |
| 4,303,961 | A | * | 12/1981 | Frosch et al. | 361/230 |
| 4,378,499 | A | * | 3/1983 | Spangler et al. | 250/287 |
| 4,417,293 | A | * | 11/1983 | Larigaldie | 361/212 |
| 4,701,941 | A | * | 10/1987 | Szirmai et al. | 378/122 |
| 4,870,284 | A | * | 9/1989 | Hashimoto et al. | 250/423 R |
| 5,021,654 | A | * | 6/1991 | Campbell et al. | 250/287 |
| 5,032,721 | A | * | 7/1991 | Bacon et al. | 250/282 |
| 5,083,019 | A | * | 1/1992 | Spangler | 250/286 |
| 5,144,127 | A | * | 9/1992 | Williams et al. | 250/287 |
| 5,154,733 | A | * | 10/1992 | Fujii et al. | 95/57 |
| 5,283,199 | A | * | 2/1994 | Bacon et al. | 436/173 |

(Continued)

FOREIGN PATENT DOCUMENTS

EP    1070960 A    1/2001

(Continued)

*Primary Examiner*—Kevin P Shaver
*Assistant Examiner*—Andrew P Bainbridge
(74) *Attorney, Agent, or Firm*—Smith Patent Office

(57) ABSTRACT

An X-ray emitting section 22 for emitting soft X-ray is arranged facing a chamber 21. An inlet duct 23 and a outlet duct 24 are arranged on both sides of the chamber 21. An irradiating region is ionized by the soft X-ray. It is therefore possible to achieve a charging device of aerosol particles that is safe and easy to handle.

6 Claims, 6 Drawing Sheets

U.S. PATENT DOCUMENTS

| | | | |
|---|---|---|---|
| 5,423,458 A * | 6/1995 | Tourigny | 222/192 |
| 5,457,316 A * | 10/1995 | Cohen et al. | 250/286 |
| 5,476,538 A | 12/1995 | Nishio et al. | |
| 5,542,964 A * | 8/1996 | Kroeger et al. | 95/6 |
| 5,545,304 A * | 8/1996 | Smith et al. | 204/603 |
| 5,656,820 A * | 8/1997 | Murakoshi et al. | 250/492.21 |
| 5,907,154 A * | 5/1999 | Shimomura | 250/288 |
| 5,907,469 A * | 5/1999 | Kim et al. | 361/225 |
| 5,973,904 A * | 10/1999 | Pui et al. | 361/225 |
| 6,103,415 A * | 8/2000 | Kurita et al. | 429/34 |
| 6,176,977 B1 * | 1/2001 | Taylor et al. | 204/176 |
| 6,194,717 B1 * | 2/2001 | Hager | 250/292 |
| 6,287,368 B1 * | 9/2001 | Ilmasti | 96/19 |
| 6,307,918 B1 * | 10/2001 | Toth et al. | 378/158 |
| 6,429,426 B1 * | 8/2002 | Doring | 250/288 |
| 6,563,110 B1 * | 5/2003 | Leri | 250/282 |
| 6,861,036 B2 * | 3/2005 | Biswas et al. | 422/186.04 |

FOREIGN PATENT DOCUMENTS

| | | |
|---|---|---|
| JP | 63-3253 A | 1/1988 |
| JP | 5-312998 A | 11/1993 |
| JP | 7-24357 A | 1/1995 |
| JP | 8-299786 A | 11/1996 |
| JP | 2951477 B | 7/1999 |
| JP | 2000-167388 A | 6/2000 |
| JP | 2001-70743 A | 3/2001 |
| JP | 2001-303134 A | 7/2001 |

* cited by examiner

F I G. 9
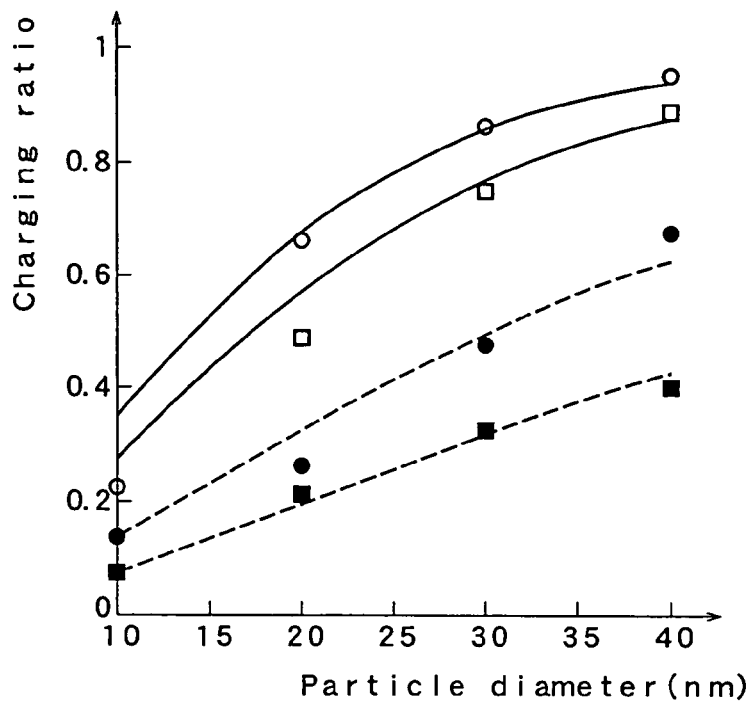
F I G. 10
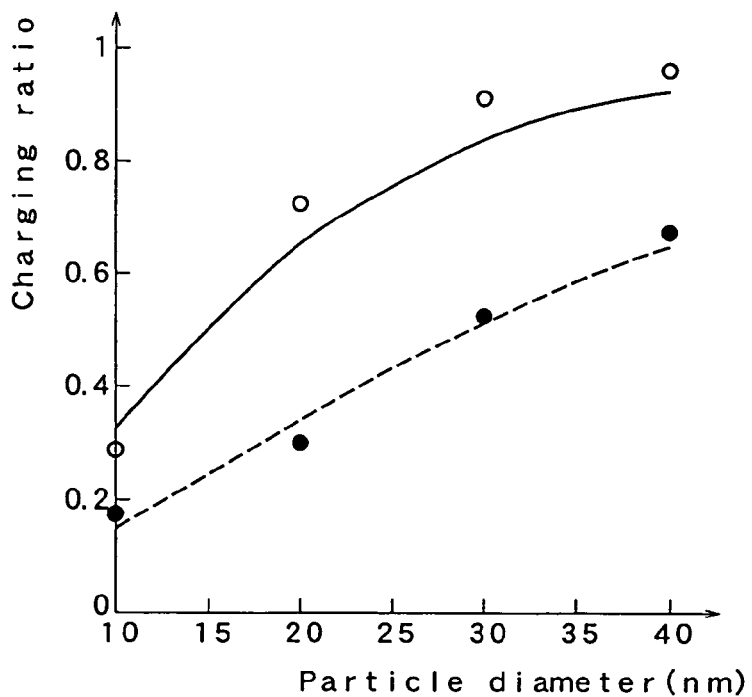

AEROSOL PARTICLE CHARGING DEVICE

TECHNICAL FIELD

The present invention relates to a charging device of aerosol particles using an X-ray source for generating a soft X-ray.

BACKGROUND ART

Recent nanotechnology is given attention regarding nanophase material since the nanophase material has a property better than a conventional material. In the nanotechnology, manufacturing, generation, transportation, deposition, and measurement of nanoparticles are essential. Charging particles or obtaining an equilibrium charged state is an effective method for controlling the nanoparticles in transportation or deposition processes. For example, the nanotechnology is used in crystal film formation by electrostatic deposition of charged colloid nanoparticles, and synthesis of two component system nanoparticles by attachment of nanosize aerosols each charged to opposite polarities. Charging of nanoparticles is indispensable in measurement of nanoparticles using static electricity such as, nanocluster DMA and particle beam mass analyzer.

Particles are normally charged as a result of impact between the gas ion and the particles. The charging state of the particles can be divided into unipolar charge and bipolar charge in accordance with the charged state. A bipolar charging device using radiation is usually used. A radiation source includes radioactive substances such as americium ($^{241}$Am), krypton ($^{85}$Kr), polonium ($^{210}$Po) and the like.

FIG. 1 is a cross sectional view showing one example of a conventional bipolar charging device using radiation. In FIG. 1, an inlet duct 2 for introducing aerosols, and a outlet duct 3 for exhausting the aerosols are provided on both ends of a cylindrical chamber 1. A radiation source 4 such as americium ($^{241}$Am) is arranged at an intermediate part of the chamber 1. Rectifying plates 5, 6 for rectifying the aerosols passing through the chamber are arranged on the left and the right. The rectifying plates 5, 6 include a plurality of fine openings, are used for rectifying the aerosols, and are arranged in the vicinity of the inlet duct 2 and the outlet duct 3, as shown in the figure. By arranging the radiation source 4 within the chamber 1 and introducing the aerosols into the chamber 1, the fine particles of the aerosols are charged by a large amount of positive and negative ions, and the equilibrium charging state can be obtained when the average charged amount is substantially zero.

Further, a charging device for generating unipolar charged ions is recently given attention for its wide range of applications. The conventional unipolar charging device, as shown in FIG. 2, includes a chamber 11 configured with a cylindrical part 12 made of resin for side surfaces, and with electrodes 13, 14 for upper and lower surfaces thereof. Voltage is applied between the upper and lower electrodes 13, 14 from a high voltage power source 15, and an ammeter 16 for measuring minute current is connected therebetween. A radiation source 17 of americium ($^{241}$Am) is arranged on the electrode 14 at the lower surface of the chamber 11. If the height of the chamber is for example, 90 mm, α ray only reaches to about 40 mm due to its range; thus, bipolar ions are generated at the lower part of the chamber. As an electric field is generated, ions of desired polarity move towards the upper part of the chamber 1. Therefore, when aerosols are flowed through the inlet duct 18, the unipolar particles are discharged from the outlet duct 19, thereby achieving unipolar charging.

The charging device using corona discharge is capable of generating unipolar or bipolar high concentration ions, and is thus widely used. According to this method, when direct current or alternating current voltage of high voltage is applied to the electrode, unipolar or bipolar ions can be generated in the vicinity of the electrode.

However, in the conventional device for charging the aerosol particles using radiation, the half-life of the radioactive substance is long and thus has a problem in terms of safety. For example, americium requires 432.2 years, and krypton ($^{85}$Kr) requires 10.72 years. Thus, management over a long period time is difficult. Further, polonium ($^{210}$Po) has a short half-life of 138 days, and thus has a problem in that the line source must be changed every few months.

Further, the conventional unipolar charging device using radiation has small generation number of ions, and has losses inside the charging device or inside a piping, and thus has a disadvantage of being difficult to use unipolar charged nanoparticles for various applications. It also has a disadvantage in that a charging operation can not be stopped when necessary.

Additionally, the charging device using corona discharge generates ozone, causes corrosion of electrodes during discharge, and generates particulate substances by the gas phase reaction at a strong electrical magnetic field, and thus has a disadvantage of polluting air. The corona discharge also has a disadvantage of generating current noise.

The present invention aims to provide a charging device of aerosol particles that is safe and easy to handle in place of the conventional charging device using radiation source or corona discharge.

DISCLOSURE OF INVENTION

According to a first aspect of the present invention, a aerosol particle charging device comprises a chamber, an inlet duct which flows gas including aerosol particles to be processed into the chamber, a outlet duct which exhausts the processed aerosols from the chamber, and an X-ray emitting section which is arranged facing the chamber and emits an X-ray having a main wavelength within a range of 0.13 nm to 2 nm.

In this aerosol particle charging device, the X-ray emitting section may include a power switch for controlling emission and stop of the X-ray.

According to a second aspect of the present invention, a aerosol particle charging device comprises a chamber, an X-ray emitting section which is arranged facing one region of the chamber and emits an X-ray having a main wavelength within a range of 0.13 nm to 2 nm, an electric field generation section which includes electrode plates arranged on both surfaces facing each other of the chamber and generates an electric field from an irradiating section to a non-irradiating section of the X-ray within the chamber, an inlet duct which is arranged in the X-ray non-irradiating section of the chamber and flows gas including aerosol particles to be processed into the chamber, and a outlet duct which is arranged at a position facing the inlet duct of the X-ray non-irradiating section of the chamber and exhausts the processed aerosols from the chamber.

In this aerosol particle charging device, the X-ray emitting section may include a power switch for controlling emission and stop of the X-ray.

BRIEF DESCRIPTION OF DRAWINGS

FIG. 9 is a graph showing change in a charging ratio with respect to a particle diameter of a positive polarity ion of this embodiment and a conventional example.

FIG. 10 is a graph showing change in a charging ratio with respect to a particle diameter of a negative polarity ion of this embodiment and the conventional example.

BEST MODE FOR CARRYING OUT THE INVENTION

Figure 1:
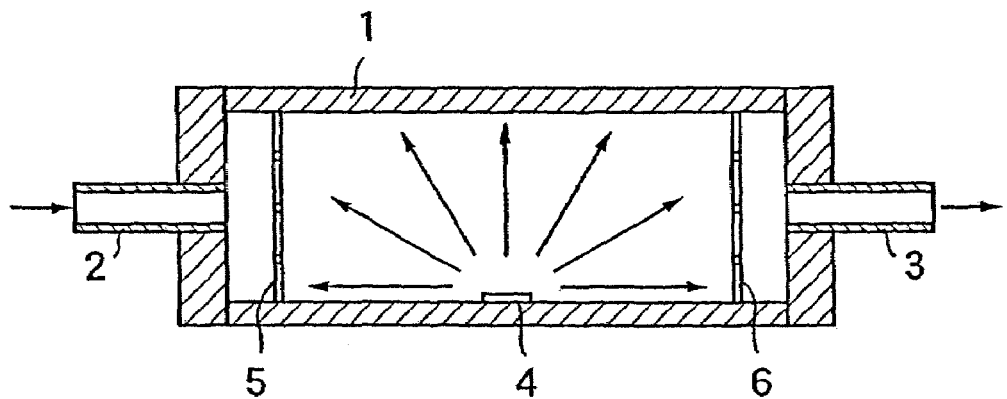
FIG. 1 is a cross sectional view showing one example of a conventional bipolar charging device of aerosol particles.
Figure 2:
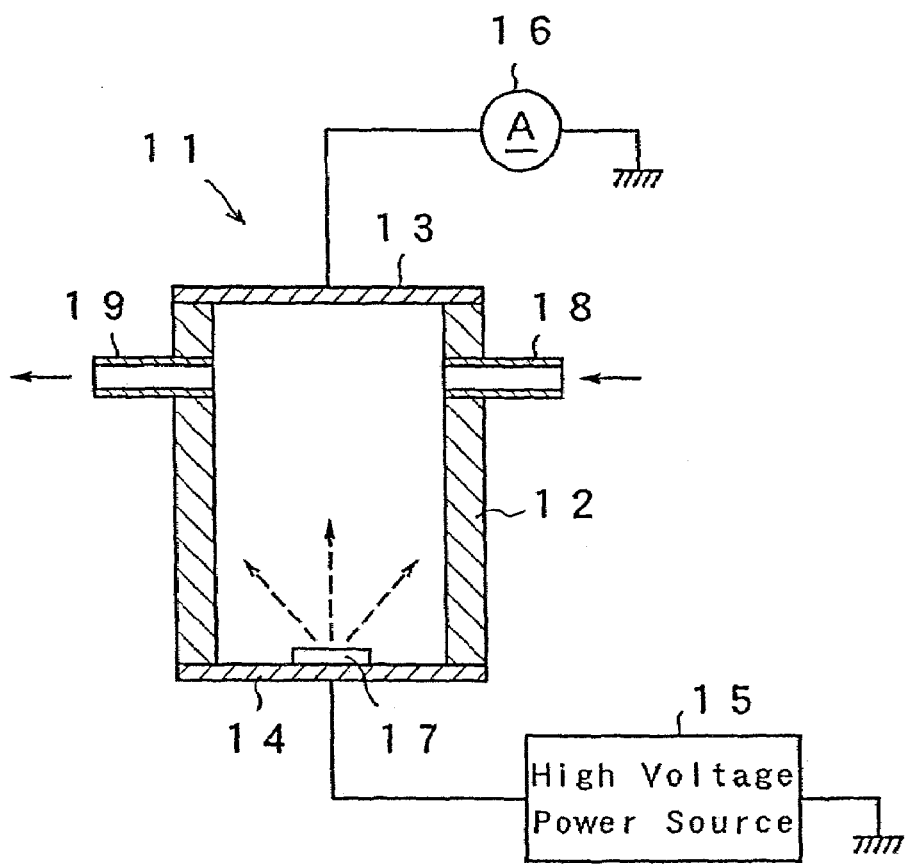
FIG. 2 is a cross sectional view showing a configuration of a conventional unipolar charging device of aerosol particles.
Figure 3:
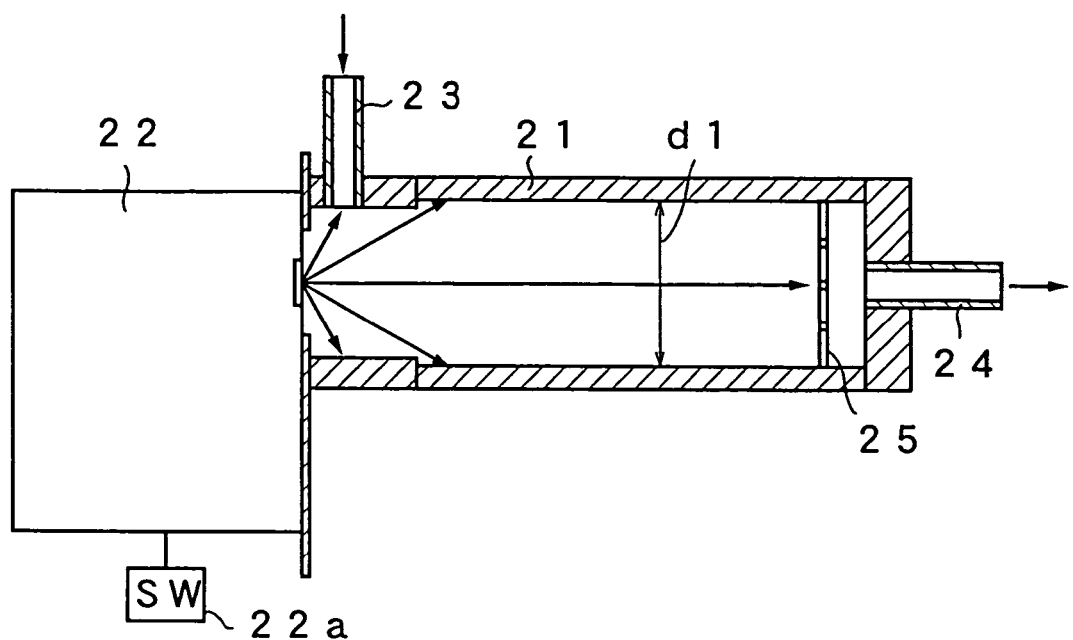
FIG. 3 is a cross sectional view showing an entire configuration of an aerosol particle charging device according to a first embodiment of the present invention.

FIG. 3 is a cross sectional view showing a configuration of a charging device of aerosol particles according to a first embodiment of the present invention. In the figure, a chamber 21 is a brass cylindrical container having an inner diameter d1 of 40 mm. An X-ray emitting section 22 is arranged at an opening at a side of the chamber 21. The X-ray emitting section 22 emits X-rays from the middle of a left end of the cylindrical chamber. An inlet duct 23 for introducing the aerosols is arranged at an upper part of the chamber 21. A outlet duct 24 for exhausting the bipolar charged aerosols is arranged at the middle of the other end of the chamber. A rectifying plate 25 having a plurality of openings for rectification is arranged in the vicinity of the outlet duct 24. Here, a distance from the X-ray emitting section 22 to the rectifying plate 25 is 90 mm.

The X-ray emitting section 22 is an X-ray source for generating a soft X-ray of 0.13 to 2 nm, and emits the X-ray at a solid angle of 120° from a window made of beryllium. Such X-ray emitting section is disclosed in, for example, Japanese Patent No. 2951477. The ions are generated across the entire emission range on a steady basis by the emission of the X-ray. If the numbers of positive and negative ions generated at the same time are unbalanced, unbalance also occurs in the charged state of the particles by one of the ions. However, according to the X-ray emitting section used in the present invention, an equivalent amount of positive and negative ions are simultaneously generated since weak X-ray is constantly irradiated. Therefore, the aerosols are neutralized without unbalance in the charging polarity. Further, ozone, electromagnetic noise, powder dust or the like does not occur. The X-ray emitting section 22 includes a power switch 22a. Emission and stop of the X-ray can be controlled by turning the power switch 22a on and off.

Figure 4:
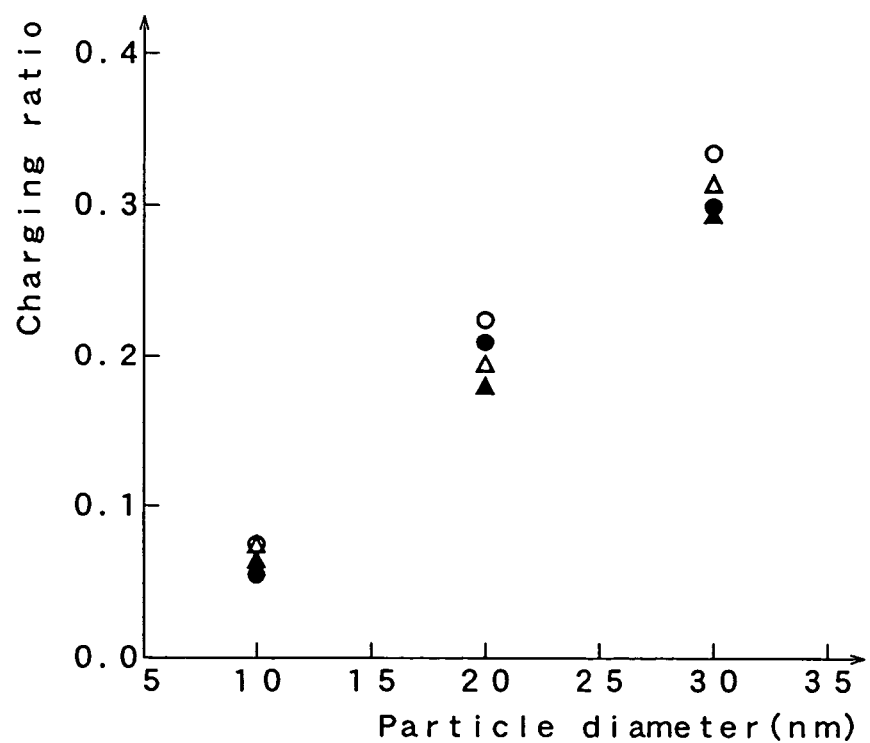
FIG. 4 is a graph showing change in a charging ratio with respect to a particle diameter.

An operation result of the aerosol particle charging device of this embodiment will now be explained using the drawings. FIG. 4 shows a ratio of the particles of relatively low concentration each having an aerosol diameter of 10 nm, 20 nm and 30 nm charged while retained in a region irradiated by the X-ray. In the figure, ▲ is a charging ratio of when a retention time is 3.2 seconds and Δ is when a retention time is 0.5 seconds in this embodiment. Moreover, ● is a case where a retention time is 3.2 seconds, and ○ is of when it is 0.5 seconds in the conventional charging device using americium as the radiation source. As seen from the figure, a charging phenomenon of the charging device using the X-ray source is a charging process similar to the conventional device using the radiation source.

Figure 5:
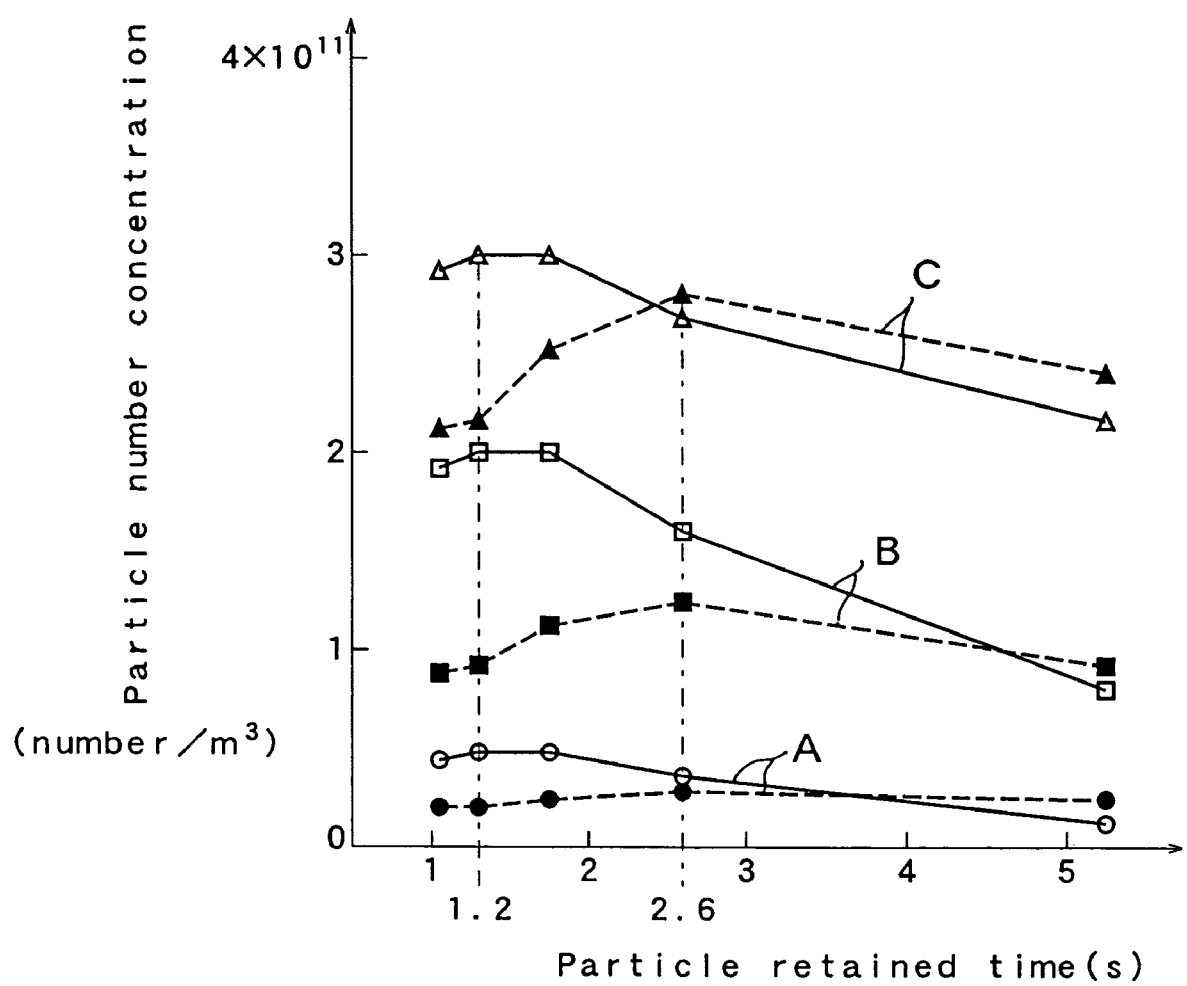
FIG. 5 is a graph showing particle retention time and charged particle number concentration of this embodiment.

FIG. 5 shows the number concentration of charged particles with respect to time retained in the chamber. A solid line is for the aerosol particle charging device using the soft X-ray according to this embodiment, and a broken line is for the conventional charging device using americium as the radiation source. A curve A is when a particle diameter is 30 nm, curve B is when a particle diameter is 50 nm, and curve C is when a particle diameter is 100 nm. As shown in the figure, in the charging device using the X-ray source, the particle number concentration reaches a peak at around 1.2 seconds regardless of the particle diameter. On the other hand, in the charging device using americium, the peak is at around 2.6 seconds. Therefore, the particles can be charged within a time shorter than the conventional device. Thus, the retention time of the particles in the chamber becomes short, and a sufficient charging can be performed to a flow of large flow rate.

The present invention is thus easy to handle and generates ions at a high concentration compared to the conventional charging device using radiation source or corona discharge. Further, bipolar ions are simultaneously generated, and thus aerosols can be neutralized.

If the power switch is arranged at the X-ray emitting section, switching can be easily performed by turning the power switch on and off, and thus has effects of being able to stop the generation of X-rays during non-operation, or to check the difference of the charging effect. For example, during an emergency or in a time of disaster of when using or storing the charging device, the radiation source may be exposed thereby causing external or internal explosion in the worst case of an emergency, disaster and the like in the charging device using the radiation source, but in the present device, safety is ensured due to a current break (automatic circuit including power switch or electric power failure). That is, safety can be ensured in handling and storage, and the X-ray can be irradiated only when necessary.

Figure 6:
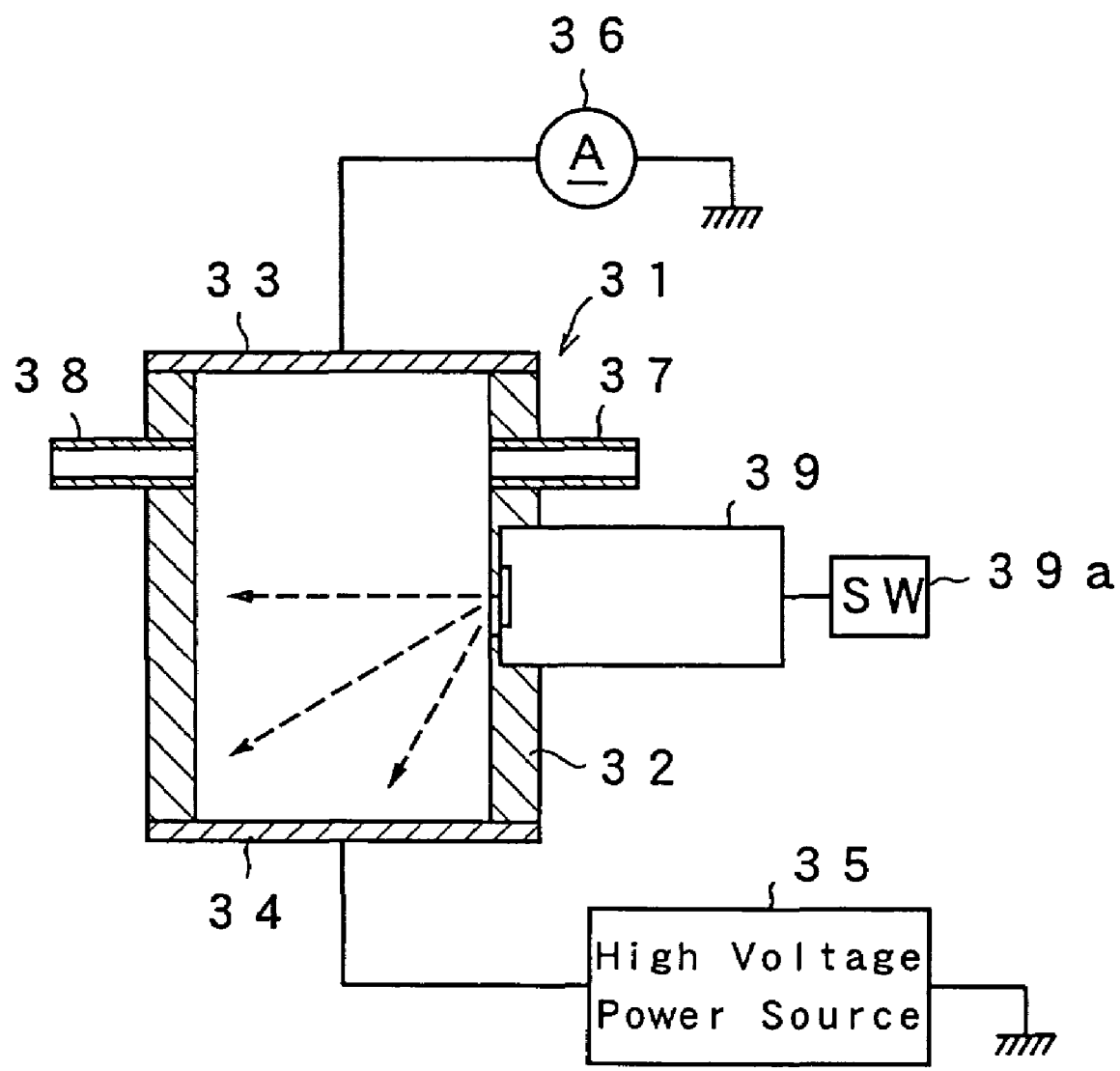
FIG. 6 is a cross sectional view showing an entire configuration of an aerosol particle charging device according to a second embodiment of the present invention.
Figure 7:
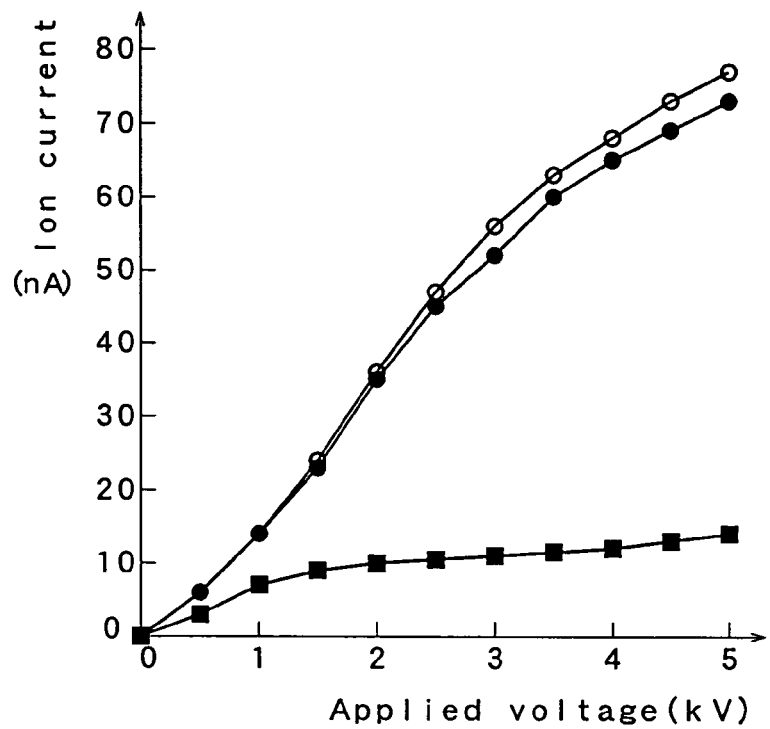
FIG. 7 is a graph showing a relationship between applied voltage and ion current in this embodiment.
Figure 8:
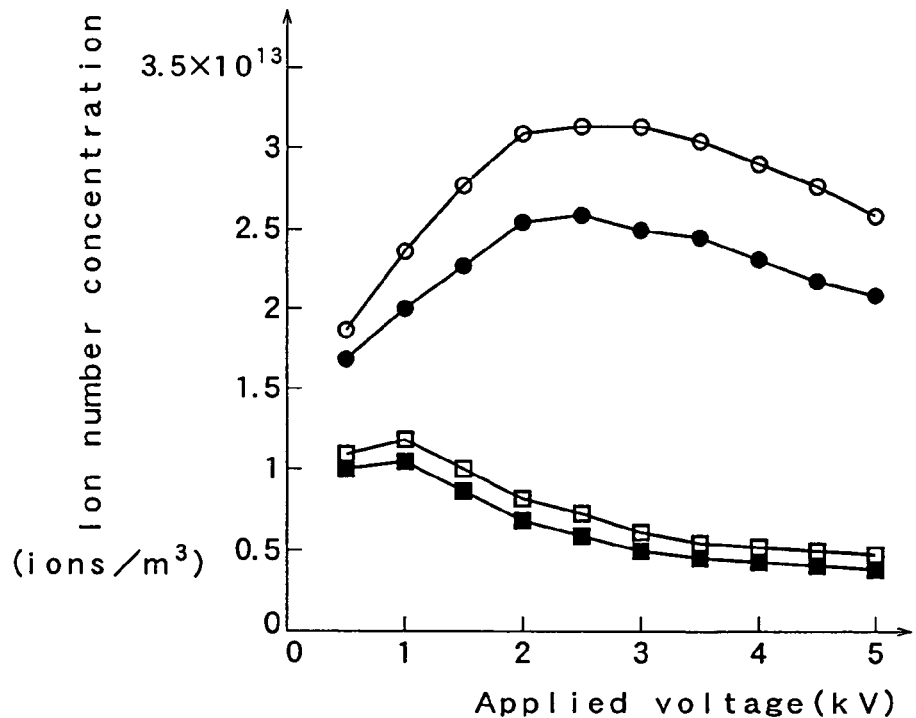
FIG. 8 is a graph showing change in ion number concentration with respect to applied voltage of this embodiment.

An unipolar aerosol particle charging device according to a second embodiment of the present invention will now be explained. FIG. 6 is a cross sectional view showing the aerosol particle charging device of this embodiment. Similar to the conventional example mentioned above, in this embodiment, the chamber 31 is formed by a cylindrical part 32 made of resin and electrodes 33, 34 made of metal such as stainless steel for the upper surface and the lower surface. A direct current high-voltage power source 35 is connected between the upper and lower electrodes 33, 34, and an ammeter 36 is connected to the electrode 33 of the upper surface. An inlet duct 37 and a outlet duct 38 are arranged on the upper part of the chamber 31 at positions facing each other.

In this embodiment, an X-ray emitting section 39 for releasing soft X-ray is arranged at substantially the middle of the chamber 31 in place of the radiation source of americium as mentioned above. The X-ray emitting section 39 is the same as that of the first embodiment mentioned above. The upper half of the opening of the X-ray emitting section 39 is covered by a side wall of the cylindrical part 32 as shown in the figure. The upper part of the opening may be covered by a shielding plate instead of the side wall. As such, the upper half of the X-ray beam is shielded, and the X-ray can be irradiated to only the lower half of the chamber 31, thereby generating positive and negative bipolar ions at the lower half of the chamber 31 by the X-ray. Further, the positive and negative ions can be separated by applying direct current high voltage to the upper and lower electrodes 33, 34 of the chamber 31. For example, if the electrode 33 is positive, the negative ions move towards the upper part of the chamber 31, and when the electrode 33 is negative, the positive ions move towards the upper part of the chamber 31. Therefore, when the aerosols are introduced from the inlet duct 37, the aerosols charged unipolar by the unipolar ion at the upper part of the chamber can be exhausted from the outlet duct 38. Thus, the unipolar charged aerosols can be exhausted by irradiating the X-ray to about ½ of the region of the chamber 31, and arranging the inlet duct and the outlet duct at the non-irradiated part not irradiated by the X-ray so as to face each other. The X-ray emitting section 39 in this embodiment also includes a power switch 39*a*. Emission and stop of the X-ray can be controlled by turning the power switch 39*a* on and off.

FIGS. 7 and 8 show results of measurement of ion current of when the same electric field is generated and the chamber is closed to measure ion generation concentration of the unipolar charging device according to this embodiment and the conventional example. In FIG. 7, ○ shows a generation property of the positive ions of the charging device using the X-ray of this embodiment, and ● shows a property of the negative ions of this embodiment of the X-ray. Herein, ■ shows a positive and negative ion generation property of the conventional unipolar charging device using americium as the radiation source. As shown in the figure, in the conventional unipolar charging device, 14 nA is obtained when the voltage is about 5 kV and is substantially saturated, but in the unipolar charging device of this embodiment, the current increases in accordance with the applied voltage, and the ion generation number is thus considered to be high. FIG. 8 shows the ion number concentration with respect to the applied voltage, where ○ is the positive ion generation property, and ● is the negative ion generation property of this embodiment. Herein, □ shows the generation property of the positive polarity ion, and ■ shows the generation property of the negative ion of the conventional device using americium as the radiation source. The difference of the positive and negative number concentration is based on the difference in the ion mobility, and in either case, the number concentration of this embodiment is high. In the unipolar charging device using americium, the peak is within a range of 0.5 to 1 KV, whereas in the X-ray charging device, the peak is between 2.5 to 3 KV.

FIGS. 9 and 10 show a charging ratio of when the particles ionize when the shown voltage is applied with respect to the particle diameter of the aerosol fine particles. FIG. 9 is for the positive ion, where ○ and □ show a charging ratio with respect to a particle diameter of when 2.5 KV and 1.0 KV is applied, respectively, in the unipolar charging device of this embodiment. On the other hand, ● and ■ show a charging ratio with respect to a particle diameter of when 0.5 KV and 3.0 KV is applied, respectively, in the conventional charging device using americium. FIG. 10 shows a generation property of the negative ion, where ○ and ● in the figure are measurement values of the charging device of when 2.5 KV and 0.5 KV are applied using the X-ray and the americium, respectively, and the solid line and the broken line show the theoretical values. As apparent from the figures, in the charging device according to this embodiment, the charging ratio increases with increase in particle diameter regardless of polarity, similar to the conventional example, and has a high charging ratio with respect to the conventional example. Thus, by using the X-ray, the unipolar charging particles can be generated at high concentration and in a short period of time. Further, the unipolar ions can be easily generated, and thus fine particles in electrostatic coating and air cleaner can be removed. The nanoparticles of high concentration are generated, and nanoparticle charging become possible and thus can be applied to manufacturing electronic application elements and the like.

When the X-ray emitting section includes the power switch, switching can be easily performed by turning on and off the power switch, and thus has effects of being able to stop the generation of X-rays during non-operation, or to check the difference of the charging effect. For example during an emergency or in a time of disaster of when using or storing the charging device, the radiation source may be exposed thereby causing external or internal explosion in the worst case of an emergency, disaster and the like in the charging device using the radiation source, but in the present device, safety is ensured due to a current break (automatic circuit including power switch or electric power failure). That is, safety in handling and storage is ensured and the X-ray is irradiated only when necessary.

In this embodiment, X-ray is irradiated to a region of about ½ of the cylindrical chamber, and the inlet duct and the outlet duct are arranged at the upper part of the chamber acting as the non-irradiated part of the X-ray, but of course, the irradiating region of the X-ray is not limited to ½, and the shape of the chamber may not necessarily be a cylinder.

INDUSTRIAL APPLICABILITY

According to the present invention, the handling can be simplified and the ions can be generated at high concentration compared to the conventional charging device using the radiation source or the corona discharge. The bipolar ions are simultaneously generated, and thus the aerosols can be neutralized.

Since the unipolar ions can be easily generated, the removal of fine particles in electrostatic coating and air washer becomes possible. The nanoparticles of high concentration can be generated, and nanoparticle charging becomes possible and thus can be applied to manufacturing of electronic application elements and the like.

The invention claimed is:

1. An aerosol particle charging device comprising:

a chamber;

an electric field generation section which includes electrode plates arranged on both surfaces facing each other in said chamber and generates an electric field from an irradiating section to a non-irradiating section within said chamber;

an X-ray emitting section which is arranged facing said chamber and emits an X-ray to said irradiating section of said chamber having a main wavelength within a range of 0.13 nm to 2 nm;

an inlet duct which is arranged in the X-ray non-irradiating section of said chamber and flows gas including aerosol particles to be processed into said chamber; and a outlet duct which is arranged at a position facing said inlet duct of the X-ray non-irradiating section of said chamber and exhausts the processed aerosols from said chamber.

2. The aerosol particle charging device according to claim 1, wherein said X-ray emitting section includes a powered switch to control the amount of or to stop the emission of the X-ray.

3. The aerosol particle charging device according to claim 2, wherein said inlet and outlet duct face each other.

4. The aerosol particle charging device according to claim 2, wherein said electric field generation section comprises a direct current high voltage power source.

5. An aerosol particle charging device comprising:
a chamber;
an inlet duct which is arranged at one end of said chamber and allows a flow of gas including aerosol particles to be processed into said chamber;
a outlet duct which is arranged at another end of said chamber and exhausts the processed aerosols from said chamber;
an X-ray emitting section which is arranged closer to said inlet duct than said outlet duct, said X-ray emitting section facing said chamber and emits an X-ray having a main wavelength within a range of 0.13 nm to 2 nm; and
a rectifying plate which is arranged closer to said outlet duct than said inlet duct in said chamber, said rectifying plate dividing said chamber into a section with said inlet duct and a section with said outlet duct, and said rectifying plate having a plurality of openings for rectifying air flow in said chamber.

6. The aerosol particle charging device according to claim 5, wherein said X-ray emitting section includes a powered switch to control the amount of or to stop the emission of the X-ray.

* * * * *